United States Patent [19]

Hasegawa et al.

[11] Patent Number: 4,615,977

[45] Date of Patent: Oct. 7, 1986

[54] METHOD FOR THE CULTIVATION OF NORMAL DIPLOID CELLS AND CULTIVATION MEDIUM USED THEREFOR

[75] Inventors: Akio Hasegawa; Sadakazu Horiguchi, both of Shizuoka, Japan

[73] Assignee: Asahi Kasei Kogyo Kabushiki Kaisha, Osaka, Japan

[21] Appl. No.: 446,144

[22] Filed: Dec. 2, 1982

[30] Foreign Application Priority Data

Dec. 24, 1981 [JP] Japan .............................. 57-212619
Aug. 24, 1982 [JP] Japan .............................. 56-145572

[51] Int. Cl.$^4$ .............................................. C12N 5/00
[52] U.S. Cl. ...................................... 435/240; 435/241
[58] Field of Search ........................ 435/240, 241, 244

[56] References Cited

U.S. PATENT DOCUMENTS

| Re. 30,985 | 6/1982 | Cartaya | 435/241 |
| 4,013,507 | 3/1977 | Rembaum | 435/241 |
| 4,017,608 | 4/1977 | Gordon | 435/240 |
| 4,055,466 | 10/1977 | Torney | 435/240 |
| 4,072,565 | 2/1978 | Weiss et al. | 435/240 |

OTHER PUBLICATIONS

Chemical Abstracts No. 13, vol. 89, Item No. 144269e, 1978.
Murakami et al. Proceedings of the National Academy of Science U.S.A., vol. 79, pp. 1158-1162, Feb. 1982.
Kano-Sueoka et al. Proceedings of the National Academy of Science U.S.A., vol. 79, pp. 5741-5744, Nov. 1979.
Iscove et al. The Journal of Experimental Medicine, vol. 147, (1978), pp. 923-933.
Maciag et al. 1980 Cell Biology International Reports, vol. 4(1), pp. 43-50.

Primary Examiner—Sam Rosen
Assistant Examiner—William J. Herald
Attorney, Agent, or Firm—Sughrue, Mion, Zinn, Macpeak, and Seas

[57] ABSTRACT

A method and medium for the multiplication of normal diploid cells from mammals is described, comprising cultivating the cells in a culture medium containing an amine derivative or derivatives represented by the general formula: $NR^1R^2R^3$ (wherein $R^1$, $R^2$ and $R^3$ represents a straight, branched or cyclic alkyl group or a hydrogen atom, provided that $R^1$, $R^2$ and $R^3$ are not hydrogen atoms at the same time. Addition of these specific amine derivatives permits multiplication of normal diploid cells in a culture medium containing a limited concentration of serum. These amine derivatives are inexpensive and can be stored for a long period of time, and their storage and handling are easy. The use of these amine derivatives overcomes various problems encountered in using serum in the multiplication of normal diploid cells according to conventional methods.

19 Claims, 5 Drawing Figures

METHOD FOR THE CULTIVATION OF NORMAL DIPLOID CELLS AND CULTIVATION MEDIUM USED THEREFOR

FIELD OF THE INVENTION

The present invention relates to a method for the cultivation of normal diploid cells from animals.

BACKGROUND OF THE INVENTION

Cultivation of animal cells has been increasingly important in both biochemical research and industrial production of hormones, vaccines, enzymes, and so forth. It is well known that in almost all of the methods of cultivating such cells it is essential for serum to be added to a culture medium. The serum, however, has disadvantages in that its supply is instable, uniform quality can be obtained only with difficulty, its storage and handling are difficult because it is liquid, and in that it is very expensive. This has seriously inhibited the development of cell cultivation in the biochemical research and the industrial production of, e.g., hormones.

In order to overcome the above-described problems, a number of investigations have been made to decrease the amount of serum necessary for cultivation by adding various kinds of hormones or proteins. Almost all of the investigations, however, are directed to a culture medium containing no serum (hereafter referred to as "serum-free culture medium") or a culture medium containing only a small amount of serum (hereinafter referred to as "low serum-content culture medium"), which are to be used in the cultivation of established cell lines and heteroploid cell lines.

Although these cells are often capable of growing limitlessly, many of them have a tumor-inducing ability and easily changeable properties. Difficulties, therefore, are encountered in their industrial application. On the other hand, normal diploid cells are cells originating from the normal tissues of animals, which have the number of chromosomes of 2n (e.g., 46 in the case of human being), undergo meiosis, and need a solid surface on which they are adsorbed. Since these normal diploid cells do not have a tumor-inducing ability and their properties are not easily changeable, they have been expected as stable cells which are suitable for use in commercial production of hormones, vaccines, enzymes, and so forth. The normal diploid cells, however, have complicated or specific nutritional requirements compared with established cell lines and heteroploid cell lines. A serum-free culture medium or a low serum-content culture medium, therefore, has not yet been established which is suitable for use in the cultivation of normal diploid cells.

SUMMARY OF THE INVENTION

As a result of extensive studies on the cultivation of normal diploid cells in a serum-free culture medium and a low serum-content culture medium, it has been found that the addition of the amine derivatives represented by the general formula: $NR^1R^2R^3$ (the symbols are as described hereinafter) to the serum-free culture medium or low serum-content culture medium greatly increases the multiplication of the cells.

The present invention, therefore, relates to a method for the cultivation of normal diploid cells originating from animals which comprises cultivating the cells in a culture medium containing an amine derivative represented by the general formula: $NR^1R^2R^3$ (wherein $R^1$, $R^2$, and $R^3$ may be the same or different, and are each an unsubstituted or substituted straight, branched or cyclic alkyl group, or a hydrogen atom, provided that they are not hydrogen atoms at the same time). The present invention also relates to a cultivation medium used therefor.

Figure 1:
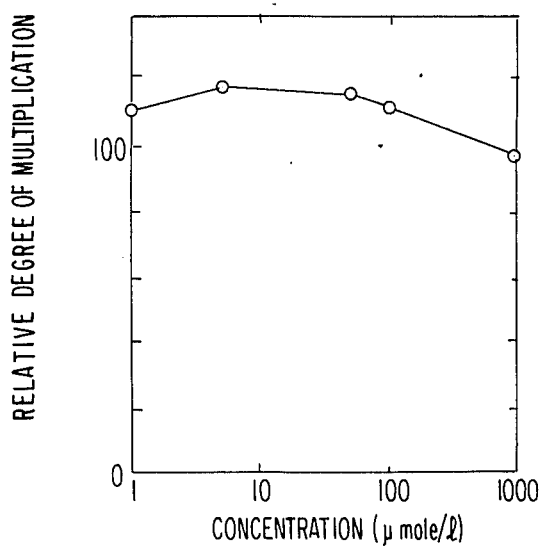
FIG. 1 is a graph demonstrating the effect of addition of ethanolamine upon the multiplication of African green monkey kidney cells.

In all the figures, the relative degree of multiplication is plotted on the ordinate with the degree of multiplication when no amine derivative is added as 100 against the concentration of amine derivative added on the abscissa.

DETAILED DESCRIPTION OF THE INVENTION

In the general formula, the straight, branched or cyclic alkyl groups represented by $R^1$, $R^2$ and $R^3$ include those having 1 to 8 carbon atom, which may be substituted with a hydroxy group, a phosphoric acid group, an amino group, and the like. Examples of the straight alkyl group include methyl group, ethyl group, n-propyl group, n-butyl group, n-pentyl group, n-hexyl group, n-heptyl group and n-octyl group. Examples of the branched alkyl group include isopropyl group, isobutyl group, isopentyl group, isohexyl group, isoheptyl group and isooctyl group. Example of the cyclic alkyl group includes cyclohexyl group. Examples of the substituted alkyl group include hydroxymethyl group, hydroxyethyl group, hydroxy-n-propyl group, hydroxyisopropyl group, hydroxy-n-butyl group, hydroxyisobutyl group, phosphohydroxymethyl group, phosphohydroxyethyl group, phosphohydroxy-n-propyl group, phosphohydroxyisopropyl group, phosphohydroxy-n-butyl group and phosphohydroxyisobutyl group.

Examples of the amines derivatives which can be used in the invention include methylamine, dimethylamine, trimethylamine, ethylamine, diethylamine, triethylamine, n-propylamine, di-n-propylamine, tri-n-propylamine, isopropylamine, diisopropylamine, tri-isopropylamine, n-butylamine, di-n-butylamine, tri-n-butylamine, isobutylamine, di-isobutylamine, tri-isobutylamine, n-pentylamine, di-n-pentylamine, tri-n-pentylamine, isopentylamine, diisopentylamine, triisopentylamine, n-hexylamine, di-n-hexylamine, tri-n-hexylamine, isohexylamine, diisohexylamine, triisohexylamine, n-heptylamine, di-n-heptylamine, tri-n-heptylamine, isoheptylamine, diisoheptylamine, triisoheptylamine, n-octylamine, di-n-octylamine, tri-n-octylamine, isooctylamine, diisooctylamine, triisooctylamine, cyclohexylamine, dicyclohexylamine, tricyclohexylamine, methanolamine, dimethanolamine, trimethanolamine, ethanolamine, diethanolamine, triethanolamine, n-propanolamine, di-n-propanolamine, tri-n-propanolamine, isopropanolamine, diisopropanolamine, triisopropanolamine, n-butanolamine, di-n-butanolamine, tri-n-butanolamine, isobutanolamine, diisobutanolamine, triisobutanolamine, phosphomethanolamine, diphosphomethanolamine, triphosphomethanolamine, phosphoethanolamine, diphosphoethanolamine, triphosphoethanolamine, phospho-n-propanolamine, diphospho-n-propanolamine, triphospho-n-propanolamine, phosphoisopropanolamine, diphosphoisopropanolamine, triphosphoisopropanolamine, phospho-n-butanolamine, diphospho-n-butanolamine, triphospho-n-butanolamine, phosphoisobutanolamine, diphosphoisobutanolamine, triphosphoisobutanolamine, ethylenediamine, diethylenetriamine, and triethylenetetramine. Of these, ethylamine, diethylamine, triethylamine, n-propylamine, di-n-propylamine, isopropylamine, diisopropylamine, triisopropylamine, n-butylamine, tri-n-hexylamine, diisoheptylamine, di-n-octylamine, tri-n-octylamine, cyclohexylamine, tricyclohexylamine, ethanolamine, diethanolamine, triethanolamine, n-propanolamine, di-n-propanolamine, isopropanolamine, n-butanolamine, di-n-butanolamine, tri-n-butanolamine, phosphoethanolamine, triphosphoethanolamine, phosphoisopropanolamine and phospho-n-butanolamine are preferably used. These amine derivatives can be used alone or in combination with each other.

A basic culture medium comprising a carbon source, a nitrogen source, inorganic salts, etc., is usually needed for cultivation of cells. This basic culture medium is necessary in the method of the invention. A number of basic culture media are known, including Minimum Essential Medium, 199 Medium, Dulbecco's Modified Eagle Medium, Ham's F-10 Medium, Ham's F-12 Medium, and RPMI 1640 Medium. In general, these basic culture media contain amino acids such as L-arginine.HCl (80–200 mg/l), L-cyoteine.HCl (20–50 mg/l), L-glutamine (100–300 mg/l), L-histidine.HCl (15–40 mg/l), L-isoleusine (4–105 mg/l), L-leusine (13–105 mg/l), L-lysine.HCl (36–146 mg/l), L-methionine (4.5–30 mg/l), L-phenylalanine (5–66 mg/l), L-threonine (12–95 mg/l), L-tryptophane (2–20 mg/l), L-tryosine (5.4–72 mg/l) and L-valine (12–94 mg/l), vitamins such as calcium panthothenate (0.01–4 mg/l), choline chloride (0.5–4 mg/l), folic acid (0.01–4.0 mg/l), inositol (0.05–35 mg/l), niacinamide (0.025–4.0 mg/l), pyridoxal.HCl (0.025–4.0 mg/l), riboflavin (0.01–0.4 mg) and thiamine.HCl (0.01–4.0 mg/l), glucose (1000–2000 mg/l and inorganic salts such as NaCl (6000–6800 mg/l), KCl (400 mg/l), $CaCl_2$ (200 mg/l), $MgCl_2.6H_2O$ (122–200 mg/l), $NaH_2PO_4$ (125–268 mg/l) and $NaHCO_3$ (1176–3700 mg/l). The compositions of these basic culture media are described in, for example Junnosuke Nakai, et al., Ed., Soshiki Baiyo (Tissue Culture), Asakura Shoten, Tokyo (1976).

In the present invention, the multiplication of normal diploid cells originating from animals such as kidney cells can be greatly stimulated in a serum-free culture medium or low-content culture medium by the addition of the amine derivatives in the culture medium. The term "low serum-content culture medium" used herein means a culture medium containing not more than about 1% by volume of serum. In particular, when the amine derivatives are added in a culture medium containing epidermal growth factor and transferrin, the multiplication of cells can be markedly stimulated, and thus it is preferred. For the purpose, epidermal growth factor is generally contained in an amount of 0.06 to 180 ng, preferably 0.3 to 37.5 ng, per 1 ml of the culture medium and transferrin is generally contained in an amount of 0.03 to 250 $\mu$g, preferably 0.4 to 50 $\mu$g, per 1 ml of the culture medium. It is further preferred that a culture medium contains 0.1 to 0.4% (V/V) serum, because the multiplication of cells can be further stimulated.

There is no particular limitation on the concentration of amine derivative added, but the multiplication of normal diploid cells can be effectively stimulated at the concentration of amine derivative of 1 to 100 $\mu$mole/l. Optimum concentration of the amine derivatives for the multiplication varies depending on the kind of amine derivatives but is independent on the presence or absence of epidermal growth factor and transferrin or the low content of serum in the culture medium.

Any normal diploid cells originating from animals can be used in the invention. Examples include human fetal kidney cells, African green monkey kidney cells, Cynomolgus monkey kidney cells, calf fetal kidney cells, rabbit kidney cells, calf fetal lung cells, human fetal skin cells, human fetal lung cells, human fetal foreskin cells, human fetal spleen cells, human fetal hypophysis cerebri cells, and human fetal euthyroid cells. The method of the present invention is particularly effective for the multiplication of human fetal kidney cells, African green monkey kidney cells, Cynomolgus monkey kidney cells, calf fetal kidney cells and rabbit kidney cells. Of these cells, human fetal lung cells can be used in the production of interferon, human fetal kidney cells can be used in the production of urokinases, and African green monkey kidney cells can be used in production of vaccines, and therefore, their industrial application value is high.

In connection with cultivation conditions and methods, those usually used in cell cultivation, for example, as described in the above-described reference, Soshiki Baiyo (Tissue Culture), can be employed. The cultivation can be performed under conditions which are usually used in the multiplication of the desired cells—e.g., at a pH of from 6 to 8, preferably from 7 to 7.5 and a temperature of from 25° to 40° C., preferably from 36° to 38° C. The pH can be controlled by performing the cultivation in air containing 5% $CO_2$ due to the buffer reaction between $CO_2$ and $NaHCO_3$ contained in a basic culture medium.

While it is necessary for normal diploid cells to be adsorbed on a solid surface for the cultivation, any of cultivation vessels usually used, e.g., cultivation dishes, cultivation flasks, roller bottles, plastic bags, spiral films, hollow fibers, capillaries, microcarriers, glass beads, and multi-layer plates, can be used in the method of the invention.

In the present invention, the normal diploid cells can be planted on a cultivation vessel at the cell population of $5 \times 10^2$ to $3 \times 10^4$ cells per 1 $cm^2$ of the adsorbed surface area of vessel, and preferably $3 \times 10^3$ to $10^4$ cells/$cm^2$.

The method of the invention overcomes various problems encountered when using a large amount of serum in the cultivation of normal diploid cells originating from animals according to the conventional methods. The amine derivatives as used herein are inexpensive compared with the serum and can be stored for long periods of time. Therefore, their storage and handling are simplified and amine derivatives having definite quality are always stably available. Furthermore, the addition of amine derivatives greatly stimulates the multiplication of cells, shortening the cultivation time and increasing the productivity of hormones, enzymes, and so forth. Thus the method of the invention is very useful in the industrial production of normal diploid cells.

The following examples are given to illustrate the invention in greater detail. However, the invention is not limited to these examples.

EXAMPLE 1

In this example, Minimum Essential Medium was used as basic culture medium. To the basic culture medium were added 15 ng/ml epidermal growth factor and 1 μg/ml transferrin, and further, a predetermined concentration of ethanolamine to prepare a culture medium.

Normal diploid cells (Flow Laboratory Co., Ltd.) originating from African green monkey kidney were suspended in the above-prepared culture medium and planted on a tissue culture dish so that the number of cells was $6\times 10^3$ per square centimeter. The cells were cultivated at 37° C. for 4 days, and thereafter, again suspended by treating with phosphate buffer physiological saline water containing 0.05% (W/V) trypsin. The number of cells was counted by the use of Coulter counter (produced by Coulter Electronics Co., Ltd.).

The results are shown in FIG. 1, in which the number of cells is plotted on the ordinate with the number of cells in a control not containing ethanolamine as 100 (degree of multiplication). The degree of multiplication in culture media containing from 1 to 100 μmole/l of ethanolamine is from 1.1 to 1.2 times that of the control. This demonstrates that the multiplication of African green monkey kidney cells is greatly enhanced.

EXAMPLE 2

In this example, the effect of ethanolamine and phosphoethanolamine upon the multiplication of normal diploid cells originating from human fetal kidney (supplied from Microbiological Associate Co., Ltd.) was examined.

The procedure of Example 1 was repeated wherein 0.4% (V/V) calf fetal serum was added to each culture medium.

Figure 2:
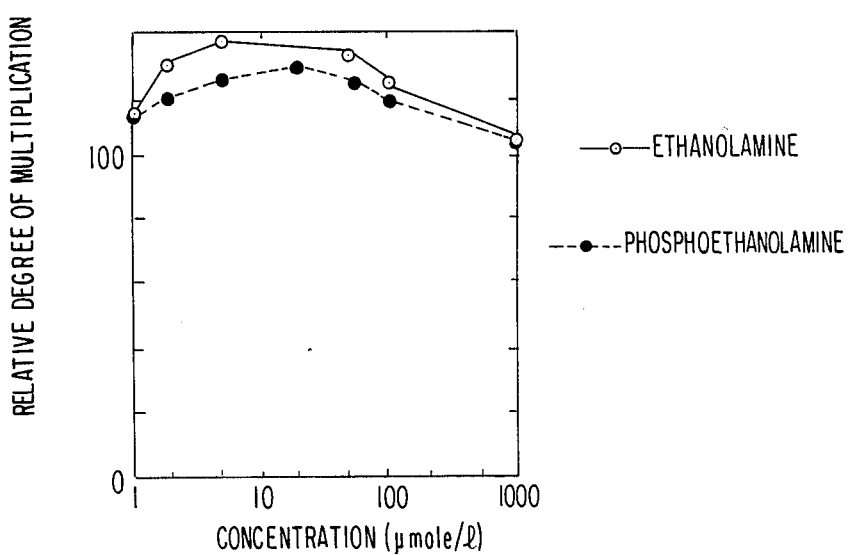
FIG. 2 is a graph demonstrating the effect of addition of ethanolamine (—o—) and phosphoethanolamine (—●—) upon the multiplication of human fetal kideny cells.

As can be seen from the results shown in FIG. 2, the addition of from 1 to 100 μmole/l of ethanolamine or phosphoethanolamine greatly enhances the multiplication of human fetal kidney cells.

For reference, the degree of multiplication was 109 where 10% (V/V) calf fetal serum was added to the basic culture medium used in Example 1 containing no amine derivative. Therefore, it can be seen that the method of the present invention achieves, using a culture medium containing as low as 0.4% (V/V) of calf fetal serum, the degree of multiplication equal to or more than that in the culture medium containing 10% (V/V) calf fetal serum.

EXAMPLE 3

In this example, Minimum Essential Medium was used as a basic culture medium. To the basic culture medium were added 15 ng/ml epidermal growth factor and 1 μg/ml transferrin, and further, a predetermined concentration of cyclohexylamine or diethanolamine to prepare a culture medium.

Normal diploid cells originating from African green monkey kidney (supplied from Flow Laboratory Co., Ltd.) were suspended in the above-prepared culture medium and planted on a tissue culture dish so that the number of cells was $6\times 10^3$ per square centimeter. The cells were cultivated at 37° C. for 4 days, and thereafter, again suspended by treating with phosphate buffer physiological saline water containing 0.05% (W/V) trypsin. The number of cells was counted by the use of Coulter counter (produced by Coulter Electronics Co., Ltd.).

Figure 3:
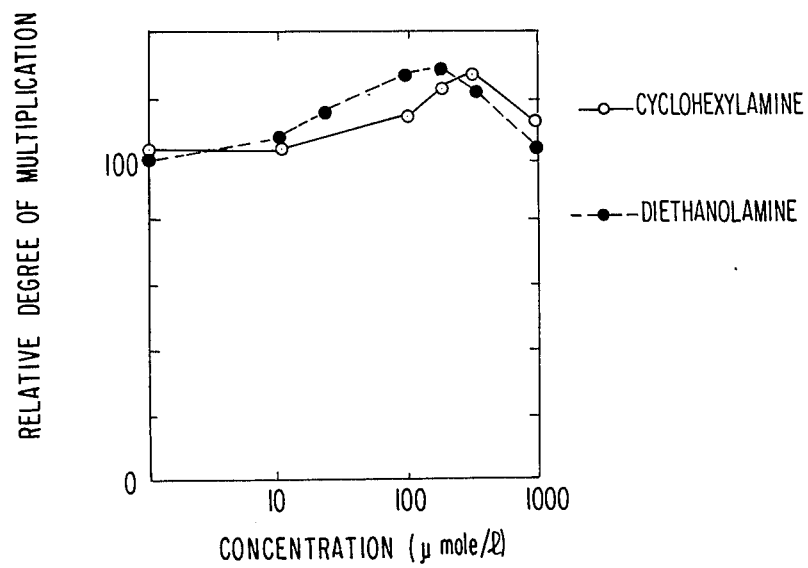
FIG. 3 is a graph demonstrating the effect of addition of cyclohexylamine (—o—) and diethanolamine (—●—upon the multiplication of African green monkey kidney cells.

The results are shown in FIG. 3, in which the number of cells is plotted on the ordinate with the number of cells in a control not containing cyclohexylamine or diethanolamine as 100 (degree of multiplication). The degree of multiplication in culture media containing from 30 to 1,000 μmole/l cyclohexylamine or diethanolamine is from 1.1 to 1.2 that of the control. This demonstrates that the multiplication of African green monkey kidney cells is greatly enhanced.

EXAMPLE 4

In this example, the effect of di-n-propylamine and diisopropanolamine upon the multiplication of normal diploid cells originating from human fetal lung (MRC-5 cells, supplied from Flow Laboratory Co., Ltd.) was examined.

The procedure of Example 1 was repeated wherein 0.4% (V/V) calf fetal serum was added to each culture medium.

Figure 4:
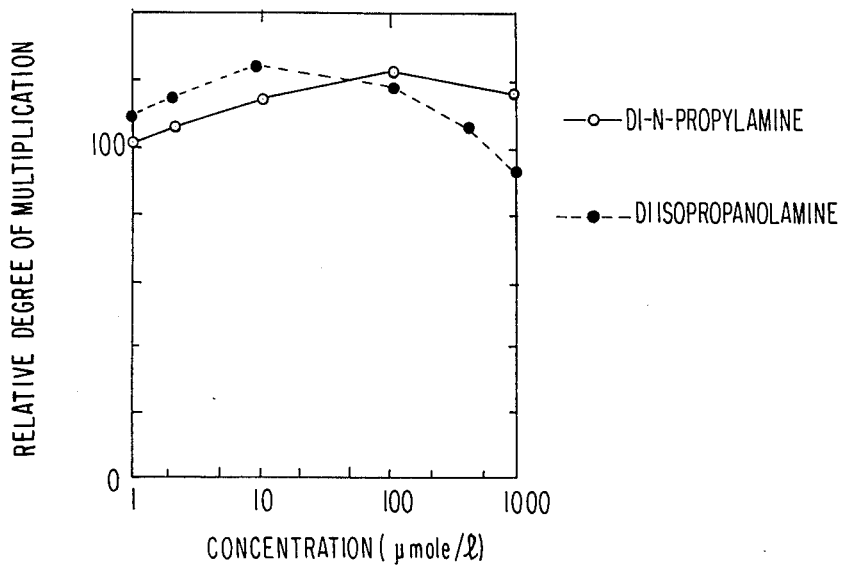
FIG. 4 is a graph demonstrating the effect of addition of di-n-propylamine (—o—) and diisopropanolamine (—●—) upon the multiplication of human fetal lung cells (MCR-5)

The results are shown in FIG. 4. As can be seen from FIG. 4, the addition of di-n-propylamine or diisopropanolamine greatly enhances the multiplication of human fetal lung cells.

EXAMPLE 5

In this example, the effect of n-octylamine, di-n-octylamine, and tri-n-octylamine upon the multiplication of normal diploid cells originating from human fetal kidney (supplied from Microbiological Associate Co., Ltd.) was examined.

The procedure of Example 1 was repeated wherein 0.4% (V/V) calf fetal serum was added to each culture medium.

Figure 5:
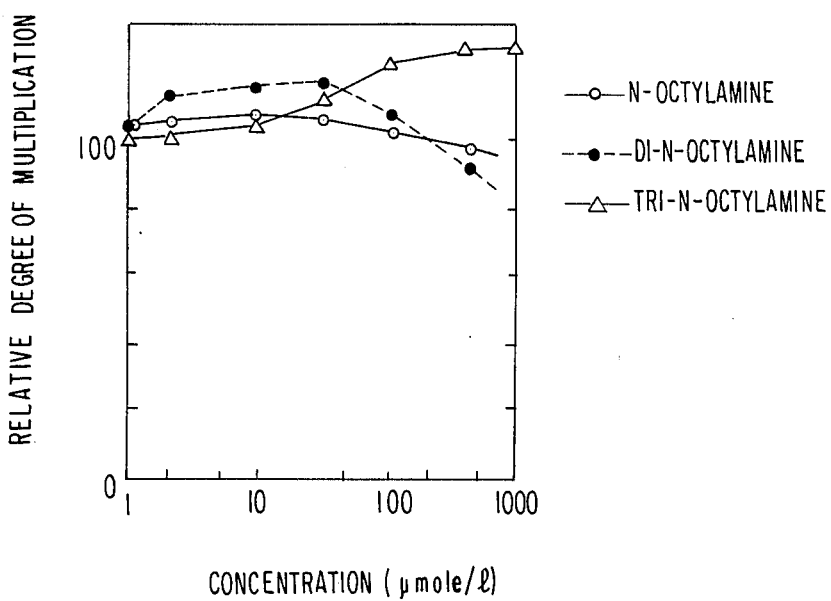
FIG. 5 is a graph demonstrating the effect of addition of n-octylamine (—o—), di-n-octylamine (—●—), and tri-n-octylamine (—Δ—) upon the multiplication of human fetal kidney cells.

As can be seen from the results shown in FIG. 5, the addition of n-octylamine, di-n-octylamine, or tri-n-octylamine greatly enhances the multiplication of human fetal kidney cells although their optimum concentrations are different.

EXAMPLE 6

In this example, the effect of isopropylamine and cyclohexylamine upon the multiplication of normal diploid cells originating from human fetal foreskin (Flow 7000 cells, supplied from Flow Laboratory Co., Ltd.) was examined.

The procedure of Example 1 was repeated wherein 0.4% (V/V) calf fetal serum was added to each culture medium.

The number of cells in a culture medium containing 30 μmole/l isopropylamine and the number of cells in a culture medium containing 300 μmole/l cyclohexylamine 1.18 times and 1.15 times, respectively, that in a culture medium containing no amine derivative. This demonstrates that both isopropylamine and cyclohexylamine have a significant effect of accelerating the multiplication of human fetal foreskin cells.

EXAMPLE 7

In this example, the effect of various kinds of alkyl group-containing amine derivatives upon the multiplication of normal diploid cells originating from human fetal kidney (supplied from Microbiological Associate Co., Ltd.) was examined.

The procedure of Example 1 was repeated wherein 0.4% (V/V) calf fetal serum was added to each culture medium.

The results are shown on Table 1, wherein the relative degree of multiplication of the cells in a culture medium containing an primary, secondary or tertiary amine is based on the degree of multiplication of the cells in a culture medium containing (epidermal growth factor and transferrin but) no amine derivative as 100.

8 carbon atoms have the effect of accelerating the multiplication of human fetal kidney cells. Further, it can also be seen that the amine derivatives have the accelerating effect regardless of the presence or absence of epidermal growth factor and transferrin.

TABLE 1

|  | Primary Amine | | Secondary Amine | | Tertiary Amine | |
| --- | --- | --- | --- | --- | --- | --- |
| Alkyl Group | Concentration* | Relative Degree of Multiplication | Concentration* | Relative Degree of Multiplication | Concentration* | Relative Degree of Multiplication |
| Methyl | 30 | 108 (75) | 30 | 110 (66) | 30 | 112 (80) |
| Ethyl | 30 | 115 (80) | 300 | 117 (71) | 300 | 115 (84) |
| n-Propyl | 30 | 124 (82) | 30 | 116 (65) | 30 | 111 (68) |
| Isopropyl | 30 | 120 (81) | 100 | 124 (82) | 100 | 118 (85) |
| n-Butyl | 100 | 115 (74) | 100 | 108 (65) | 100 | 109 (81) |
| Isobutyl | 100 | 112 (74) | 100 | 112 (70) | 100 | 108 (71) |
| n-Pentyl | 100 | 102 (65) | 100 | 103 (70) | 100 | 109 (72) |
| Isopentyl | 100 | 108 (66) | 100 | 110 (72) | 100 | 101 (56) |
| n-Hexyl | 100 | 110 (70) | 100 | 112 (66) | 300 | 115 (68) |
| Isohexyl | 100 | 108 (71) | 100 | 109 (68) | 300 | 109 (70) |
| n-Heptyl | 100 | 105 (65) | 100 | 109 (71) | 300 | 112 (71) |
| Isoheptyl | 100 | 112 (72) | 100 | 115 (75) | 300 | 111 (66) |
| n-Octyl | 30 | 103 (70) | 30 | 115 (79) | 300 | 120 (85) |
| Isoctyl | 30 | 106 (71) | 30 | 105 (62) | 300 | 112 (79) |
| n-Dodecyl | 100 | 99 (40) | — | — (—) | — | — (—) |
| n-Tetradecyl | 100 | 95 (48) | — | — (—) | — | — (—) |
| n-Hexadecyl | 100 | 98 (44) | — | — (—) | — | — (—) |
| Cyclohexyl | 300 | 120 (82) | 300 | 112 (68) | 300 | 115 (79) |

[Note]
—: not tested
*μmole/l

EXAMPLE 8

In this example, the effect of amine derivatives containing a substituted alkyl group upon the multiplication of normal diploid cells originating from human fetal lung (MRC-5 cells, supplied from Flow Laboratory Co. Ltd.) was examined.

The procedure of Example 7 was repeated and the results are shown in Table 2.

The degree of multiplication was about 1.1 to 1.2 times the control. This demonstrates that the addition of the amine derivatives greatly enhance the multiplication of normal diploid cells, i.e., MRC-5 cells.

TABLE 2

|  | Primary Amine | | Secondary Amine | | Tertiary Amine | |
| --- | --- | --- | --- | --- | --- | --- |
| Substituted Alkyl Group | Concentration* | Relative Degree of Multiplication | Concentration* | Relative Degree of Multiplication | Concentration* | Relative Degree of Multiplication |
| Hydroxymethyl | 30 | 109 | 100 | 112 | 100 | 110 |
| Hydroxyethyl | 30 | 112 | 100 | 122 | 100 | 118 |
| Hydroxy-n-propyl | 30 | 123 | 30 | 115 | 100 | 114 |
| Hydroxyisopropyl | 30 | 121 | 100 | 111 | 100 | 105 |
| Hydroxy-n-butyl | 100 | 118 | 300 | 120 | 300 | 121 |
| Hydroxyisobutyl | 300 | 105 | 300 | 112 | 300 | 110 |
| Phosphohydroxymethyl | 30 | 112 | 30 | 110 | 100 | 110 |
| Phosphohydroxyethyl | 30 | 114 | 30 | 110 | 100 | 115 |
| Phosphohydroxypropyl | 100 | 111 | 100 | 108 | 100 | 113 |
| Phosphohydroxyisopropyl | 100 | 120 | 100 | 105 | 100 | 108 |
| Phosphohydroxy-n-butyl | 300 | 115 | 300 | 110 | 300 | 111 |
| Phosphohydroxyisobutyl | 300 | 105 | 300 | 108 | 300 | 107 |
| Aminoethyl | 300 | 110 | — | — | | |

[Note]
*μmole/l

The concentrations of the amine derivatives aded to the culture media are shown in Table 1. The values in the parentheses in Table 1 indicate a relative degree of multiplication of the cells in a culture medium containing no epidermal growth and transferrin. It was also found that a relative degree of multiplication was 42 in a culture medium containing no epidermal growth factor, transferrin and amine derivative.

It can be seen that all primary, secondary, and tertiary amines containing an alkyl group having from 1 to While the invention has been described in detail and with reference to specific embodiments thereof, it will be apparent to one skilled in the art that various changes and modifications can be made therein without departing from the spirit and scope thereof.

What is claimed is:

1. A method for the cultivation of normal diploid cells originating from mammals, comprising the steps of:
   (A) providing a basic culture medium for normal diploid cells originating from mammals comprising a carbon source, a nitrogen source, inorganic salts and, as additional components, 0.06 to 180 ng/ml of epidermal growth factor, 0.03 to 250 μg/ml of transferrin, 0.1 to 0.4% by volume of serum and an amine derivative or derivatives represented by the general formula: $NR^1R^2R^3$ wherein $R^1$, $R^2$ and $R^3$ may be the same or different, and each is a hydrogen atom or an unsubstituted or substituted straight, branched or cyclic alkyl group of 1 to 8 carbon atoms, wherein the substituent for the substituted alkyl group is a hydroxyl group, a phosphoric acid group or an amino group, provided that $R^1$, $R^2$ and $R^3$ are not hydrogen atoms at the same time;
   (B) providing normal diploid cells originating from mammals on a surface of the culture medium; and
   (C) allowing the cells to grow.

2. A method as claimed in claim 1, wherein $R^1$, $R^2$, and $R^3$ are the same.

3. A method as claimed in claim 1, wherein the straight alkyl group is a methyl group, an ethyl group, a n-propyl group, a n-butyl group, a n-pentyl group, a n-hexyl group, a n-heptyl group, or a n-octyl group.

4. A method as claimed in claim 1, wherein the branched alkyl group is an isopropyl group, an isobutyl group, an isopentyl group, an isohexyl group, an isoheptyl group, or an isooctyl group.

5. A method as claimed in claim 1, wherein the cyclic alkyl group is a cyclohexyl group.

6. A method as claimed in claim 1, wherein the substituted alkyl group is a hydroxymethyl group, a hydroxyethyl group, a hydroxy-n-propyl group, a hydroxyisopropyl group, a hydroxy-n-butyl group, a hydroxyisobutyl group, a phosphohydroxymethyl group, a phosphohydroxyethyl group, a phosphohydroxy-n-propyl group, a phosphohydroxyisopropyl group, a phosphohydroxy-n-butyl group, or a phosphohydroxyisobutyl group.

7. A method as claimed in claim 1, wherein the amine derivative or derivatives contained in the culture medium are at a concentration of 1 to 1000 μmole/l.

8. A method as claimed in claim 1, wherein the normal diploid cells originating from mammels are normal diploid cells originating from kidney.

9. A method as claimed in claim 8, wherein the kidney is human fetal kidney.

10. A method as claimed in claim 1, wherein the normal diploid cells originating from mammals are normal diploid cells originating from human fetal lung.

11. A method as claimed in claim 1, wherein the normal diploid cells originating from mammals are normal diploid cells originating from human fetal foreskin.

12. The method for cultivation of normal diploid cells as claimed in claim 1, wherein said basic culture medium is selected from the group consisting of Minimum Essential Medium, 199 Medium Dulbecco's Modified Eagle Medium, Ham's F-10 Medium, Ham's F-12 Medium and RPMI 1640 Medium.

13. A method of the cultivation of normal diploid cells as claimed in claim 1, wherein said normal diploid cells are cells originating from normal tissues of mammals, and wherein said cells have the number of chromosomes of 2n, undergo meiosis and need a solid surface for growth on which the cells are adsorbed.

14. A method for cultivation of normal diploid cells as claimed in claim 1, wherein said normal diploid cells are selected from the group consisting of human fetal kidney cells, African green monkey kidney cells, Cynomologus monkey kidney cells, calf fetal kidney cells, rabbit kidney cells, calf fetal lung cells, human fetal skin cells, human fetal lung cells, human fetal foreskin cells, human fetal spleen cells, human fetal hypophysis cerebri cells and human fetal euthyroid cells.

15. A cultivation medium for normal diploid cells originating from mammals, comprising a basic cultivation medium for normal diploid cells originating from mammals comprising a carbon source, a nitrogen source, inorganic salts and, as additional components, 0.06 to 180 ng/ml of epidermal growth factor, 0.03 to 250 μg/ml of transferrin, 0.1 to 0.4% by volume of serum and an amine derivative or derivatives represented by the general formula: $NR^1R^2R^3$ wherein $R^1$, $R^2$ and $R^3$ may be the same or different, and each is a hydrogen atom or an unsubstituted or substituted straight, branched or cyclic alkyl group of 1 to 8 carbon atoms, wherein the substituent for the substituted alkyl group is a hydroxyl group, a phosphoric acid group or an amino group, provided that $R^1$, $R^2$ and $R^3$ are not hydrogen atoms at the same time.

16. The cultivation medium for normal diploid cells as claimed in claim 15, wherein said basic culture medium is selected from the group consisting of Minimum Essential Medium, 199 Medium, Dulbecco's Modified Eagle Medium, Ham's F-10 Medium, Ham's F-12 Medium and RPMI 1640 Medium.

17. A cultivation medium for normal diploid cells as claimed in claim 15, wherein said normal diploid cells are cells originating from normal tissues of mammals, and wherein said cells have the number of chromosomes of 2n, undergo meiosis and need a solid surface for growth on which the cells are adsorbed.

18. A method for cultivation of normal diploid cells as claimed in claim 15, wherein said normal diploid cells are selected from the group consisting of human fetal kidney cells, African green monkey kidney cells, Cynomolgus monkey kidney cells, calf fetal kidney cells, rabbit kidney cells, calf fetal lung cells, human fetal skin cells, human fetal lung cells, human fetal foreskin cells, human fetal spleen cells, human fetal hypophysis cerebri cells and human fetal euthyroid cells.

19. The cultivation medium as claimed in claim 15, wherein the amine derivative or derivatives contained in the cultivation medium are at a concentration of 1 to 1000 μmole/l.

* * * * *